(12) United States Patent
Chen (10) Patent No.: US 8,106,108 B2
(45) Date of Patent: Jan. 31, 2012

(54) ULTRAVIOLET LIGHT ABSORBING OPTICAL ELEMENTS AND COMPOSITIONS AND METHODS FOR MANUFACTURE (75) Inventor: Fang Chen, Hallet Cove (AU)

(73) Assignee: Carl Zeiss Vision Australia Holdings Limited, Lonsdale (AU)

(*) Notice: Subject to any disclaimer, the term of this patent is extended or adjusted under 35 U.S.C. 154(b) by 0 days.

(21) Appl. No.: 12/440,104

(22) PCT Filed: Aug. 30, 2007

(86) PCT No.: PCT/AU2007/001263
§ 371 (c)(1),
(2), (4) Date: Apr. 14, 2009

(87) PCT Pub. No.: WO2008/028217
PCT Pub. Date: Mar. 13, 2008

(65) Prior Publication Data
US 2010/0041787 A1  Feb. 18, 2010

(30) Foreign Application Priority Data
Sep. 6, 2006  (AU) ............................... 2006904855

(51) Int. Cl.
G02B 1/04 (2006.01)
G02C 7/10 (2006.01)

(52) U.S. Cl. ........................................ 523/106; 351/163

(58) Field of Classification Search .................. 523/106
See application file for complete search history.

(56) References Cited

U.S. PATENT DOCUMENTS

| 3,118,887 A | 1/1964 | Hardy et al. |
| 3,268,474 A | 8/1966 | Hardy et al. |
| 5,098,445 A * | 3/1992 | Hung et al. ........................ 8/507 |
| 5,621,052 A | 4/1997 | Szita et al. |
| 5,760,228 A | 6/1998 | Waterman |
| 6,239,275 B1 | 5/2001 | Gupta et al. |
| 6,297,378 B1 | 10/2001 | Gupta et al. |
| 6,867,250 B1 * | 3/2005 | Gupta et al. .................. 524/100 |
| 2003/0094714 A1 * | 5/2003 | Buazza et al. ................. 264/1.38 |
| 2004/0236064 A1 * | 11/2004 | Ooga et al. .................... 528/300 |
| 2006/0073280 A1 * | 4/2006 | Bauer et al. ................. 427/372.2 |
| 2006/0083940 A1 * | 4/2006 | Bekele ........................ 428/474.4 |

FOREIGN PATENT DOCUMENTS

| CN | 1278799 A | 1/2001 |
| JP | 2000-147201 A | 5/2000 |
| JP | 2006-089535 A | 4/2006 |
| WO | WO 97/20247 A1 | 6/1997 |
| WO | WO 99/26934 A1 | 6/1999 |
| WO | WO 99/26935 A1 | 6/1999 |

OTHER PUBLICATIONS

Form PCT/ISA/210 International Search Re.ort dated Nov. 7, 2007.
English Translation of Notification of the First Office Action dated Aug. 4, 2010 for Chinese Patent Application No. 200780036467.X.

* cited by examiner

*Primary Examiner* — Mark Eashoo
*Assistant Examiner* — David Karst
(74) *Attorney, Agent, or Firm* — Buchanan Ingersoll & Rooney, P.C.

(57) ABSTRACT

The present invention relates to a UV absorbing optical element comprising a polymer optical element substrate, and a UV light absorbing amount of a tris-aryltriazine-based UV absorber incorporated in said substrate. The present invention also provides a method for forming a UV absorbing optical element.

19 Claims, 5 Drawing Sheets

ULTRAVIOLET LIGHT ABSORBING OPTICAL ELEMENTS AND COMPOSITIONS AND METHODS FOR MANUFACTURE

This application claims priority from Australian Provisional Patent Application No. 2006904855 filed on 6 Sep. 2006, the contents of which are to be taken as incorporated herein by this reference.

FIELD OF THE INVENTION

The present invention relates to ultraviolet (UV) light absorbing plastic optical elements, and compositions and methods for making such optical elements. More specifically, the invention relates to plastic optical elements which absorb long-wave UV light having a wavelength up to around 380 nm to 400 nm, and to compositions and methods for making such optical elements.

It will become apparent from the following description that the present invention was developed in relation to the manufacture of lenses. However, it will also be apparent that there may be applications for the invention in other fields in which UV blocking transparent optical materials are required.

BACKGROUND OF THE INVENTION

UV light having a wavelength of 200 nm to 400 nm can have damaging short-term and long-term effects on the eye. For example, absorption of UV light, especially higher wavelength UV light, by the retina is believed to accelerate or cause retinal injuries such as macular degeneration.

In the field of lenses, such as ophthalmic lenses and sunglass lenses, there is a demand for lenses that protect human eyes from UV light. The addition of UV light absorbing compounds ('UV absorbers') in lenses to minimise any detrimental effects of UV light by absorbing light in the region of 290 nm to 400 nm is known.

Plastic optical elements, such as lenses and the like, are commonly manufactured from transparent plastic materials, such as polymers based on diethylene glycol bisallylcarbonate monomers, and polycarbonates. Various methods are known for producing UV light absorbing plastic optical elements, including:
(i) Incorporation of a UV absorber into a monomer followed by polymerising the monomer to give the plastic optical element.
(ii) Imbibing plastic optical elements with a UV absorber by dipping a formed plastic optical element in a solution containing a UV absorber so that the UV absorber is imbibed into the optical element.
(iii) Incorporating a UV absorber in a hard coating on a surface of the plastic optical element.

Commonly used UV absorbers for plastic lenses in particular are benzophenones and benzotriazoles and their derivatives, such as those having the following structures:

2,2'-dihydroxy-4-methoxy benzophenone (Cyasorb UV24)

2-(2H-benzotriazol-2-yl)-4,6-ditertpentylphenol (Tinuvin 328)

A large number of commercially available plastic lenses capable of absorbing UV light are produced according to the imbibition method mentioned above. However, the imbibition results in an extra step in the manufacturing process. Furthermore, it can be difficult to accurately control the amount of UV absorber that is incorporated into a lens using this method. As to the third method mentioned above, limitations on the thickness of hard coatings means that relatively high concentrations of UV absorber are required to provide a UV cutoff above about 380 nm. However, the abrasion resistance of a hard coat is often compromised at such high concentrations.

As a result of the aforementioned difficulties with the second and third methods, the first method has become a conventional method of fabricating plastic lenses with UV protection.

Plastic lenses based on diethylene glycol bisallylcarbonate (CR-39) monomers in particular are in widespread use. However, there have been problems incorporating UV absorbers into CR-39 lenses, principally because the initiators used to polymerise the CR-39 monomers can also react with UV absorbers that are present in the monomer mixture. More particularly, a high concentration of a peroxide initiator such as diisopropyl peroxydicarbonate (also called isopropyl peroxide (IPP)), dicyclohexyl peroxydicarbonate or benzoyl peroxide is needed to polymerise the monomer. The concentration typically used is around 3% by weight. However, these initiators are also oxidizing reagents that can react with the UV absorber, thereby reducing the effective concentration of the initiator which leads to incomplete polymerisation. This results in a variety of lens defects including softness and/or yellowing.

An additional problem associated with the use of UV absorbers in CR-39 lenses in particular is that the lenses produced are often extremely yellowish, resulting in a poor appearance.

There is a need for compositions and methods for manufacturing optical elements, such as lenses, that are capable of absorbing UV light having in the wavelength range of 300 nm up to 380-400 nm without the lens being unacceptably soft or yellow.

Throughout this specification reference may be made to documents for the purpose of describing various aspects of the invention. However, no admission is made that any reference cited in this specification constitutes prior art. In particular, it will be understood that the reference to any document herein does not constitute an admission that any of these documents forms part of the common general knowledge in the art in any country.

Throughout the description and claims of this specification, the word "comprise" and variations of the word, such as "comprising" and "comprises", is not intended to exclude other additives, components, integers or steps.

SUMMARY OF THE INVENTION

The present invention arises from our finding that tris-aryltriazine-based UV absorbers can be incorporated into lens substrate monomer compositions in amounts sufficient to absorb UV light having wavelength from 300 nm up to 380-400 nm in a finished lens after polymerisation without substantially affecting formation of the lens. Furthermore, we found that tris-aryltriazine-based UV absorbers can be used without leading to commercially unacceptable yellowing of a lens. We found that tris-aryltriazine-based UV absorbers have superior properties in certain plastic lenses, particularly in CR-39 or CR-39/allyl-based polymer lenses.

The present invention provides a UV absorbing optical element comprising a polymer optical element substrate, and a UV light absorbing amount of a tris-aryltriazine-based UV absorber incorporated in said substrate.

The present invention also provides an optical material comprising a UV light absorbing amount of a tris-aryltriazine-based UV absorber incorporated in a polymer optical element substrate.

The present invention also provides a casting composition capable of being polymerised to form a UV absorbing optical element, the composition comprising an optical element substrate monomer, and a UV absorbing amount of a tris-aryltriazine-based UV absorber.

The present invention also provides a method for forming a UV absorbing optical element, the method comprising combining a UV absorbing amount of a tris-aryltriazine-based UV absorber with an optical element substrate monomer and polymerising the monomer. The method could further comprise introducing the mixture into a mold for a lens before polymerising the monomer.

In an embodiment, the UV absorbing amount of a tris-aryltriazine-based UV absorber is sufficient to absorb long-wave UV light having a wavelength up to around 380 nm to 400 nm. In one embodiment, the % transmittance of light having a wavelength of 380 nm for a 2 mm thick sample of the optical element is less than 20%. In another embodiment, the % transmittance of light having a wavelength of 380 nm for a 2 mm thick sample of the optical element is less than 10%. In a further embodiment, the % transmittance of light having a wavelength of 380 nm for a 2 mm thick sample of the optical element is less than 2%.

In an embodiment, the % transmittance of light having a wavelength of 400 nm for a 2 mm thick sample of the optical element is less than 70%.

In an embodiment, the optical element is a lens element, such as a lens for spectacles or sunglasses. It will be evident that, in this embodiment, the optical element substrate is the lens itself.

We have found that tris-aryltriazine-based UV absorbers can be incorporated into a variety of polymer lens substrates to produce lenses having an excellent ability to absorb UV light in the wavelength range of 300 nm up to 380-400 nm without resulting in a lens that is unacceptably yellow in colour.

The tris-aryltriazine-based UV absorber may be a compound according to Formula (I):

Formula (I)

wherein:
each $Ar^1$, $Ar^2$, and $Ar^3$ is independently selected from the group consisting of: aryl and heteroaryl, each of which may be optionally substituted.

In an embodiment, the tris-aryltriazine-based UV absorber is a compound according to Formula (II):

Formula (II)

wherein:
each $R^1$, $R^3$, and $R^5$ is independently selected from the group consisting of: hydrogen, optionally substituted alkyl, optionally substituted alkenyl, optionally substituted alkynyl, optionally substituted aryl, optionally substituted heteroaryl, optionally substituted heterocyclyl, optionally substituted acyl, optionally substituted alkoxy, optionally substituted alkenoxy, optionally substituted alkynoxy, optionally substituted acyloxy, optionally substituted thioalkyl, carboxyl, carboxy ester, and amido;

each $R^2$, $R^4$, and $R^6$ is independently selected from the group consisting of: hydrogen, halogen (F, Cl, Br, I), optionally substituted alkyl, optionally substituted alkenyl, optionally substituted alkynyl, optionally substituted aryl, optionally substituted heteroaryl, optionally substituted heterocyclyl, acyl, thio, optionally substituted thioalkyl, carboxyl, carboxy ester, amino, amido, cyano, and nitro; and each m, n, o, w, x, and y is an integer independently selected from the group consisting of 0, 1, 2, 3, 4, and 5, provided that each m+w, n+x, and o+y is an integer selected from the group consisting of 0, 1, 2, 3, 4, and 5.

In an embodiment, the monomer is a diethylene glycol bisallylcarbonate (CR-39™) monomer and a 2 mm thick sample of the optical element has a yellowness index (YI) of less than about 2.0 and a % transmittance of light at 380 nm of less than about 20%.

In another embodiment, the monomer is a mixture of diethylene glycol bisallylcarbonate (CR-39™) monomer and an allyl monomer selected from one or more of the group consisting of: diallyl phthalate (DAP), diallyl isophthalate (DAIP), and diallyl terephthalate (DATP) monomers and a 2 mm thick sample of the optical element has a yellowness index (YI) of less than about 2.0 and a % transmittance of light at 380 nm of less than about 20%.

In another embodiment, the monomer is an ethoxylated bisphenol A dimethacrylate monomer and a 2 mm thick sample of the optical element has a yellowness index (YI) of less than about 2.0 and a % transmittance of light at 380 nm of less than about 10%.

GENERAL DESCRIPTION OF THE INVENTION

The present invention, and embodiments thereof, will now be described in more detail. However, before proceeding it is important to note that various terms that will be used throughout the specification have meanings that will be well understood by a skilled addressee. However, for ease of reference, some of these terms will now be defined.

The term "optical element" refers generally to any optical transparent material and includes lenses (including ophthalmic lenses), lens blanks, camera lenses, instrument lenses, window panes, transparent display panels, and the like.

The term "lens" refers generally to a finished or unfinished lens or lens blank manufactured from an optically transparent plastic material. Plastic materials useful in preparation of lenses are well known in the art and include, by way of example, polycarbonates, polymethacrylates, and the like.

The term "polymer" refers generally to a homopolymer, which is formed from the same monomeric units, or a copolymer, which is formed from two or more different monomeric units.

The term "polymer optical element substrate" when used in relation to an optical element refers generally to the bulk material which forms the optical element. Unless stated otherwise, the substrate excludes any coatings on the substrate. For example, ophthalmic lenses are typically coated with one or more functional layers, such as abrasion resistant layers, anti-reflection layers, etc. These coatings are usually in the form of discrete layers on the lens substrate and are not considered herein to be part of the optical element substrate unless expressly stated otherwise.

The term "tris-aryltriazine-based" refers generally to a compound having a 1,3,5-triazine core structure with three aromatic moieties bonded to carbons at the 2, 4, and 6 positions. Accordingly, the structural formula for an unsubstituted or underivatised tris-aryltriazine is:

The term "aryl" as a group or part of a group refers generally to: (i) an optionally substituted monocyclic, or fused polycyclic, aromatic carbocycle (ring structure having ring atoms that are all carbon) preferably having from 5 to 12 atoms per ring. Non-limiting examples of aryl groups include phenyl, naphthyl, and the like; and (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl.

The term "heteroaryl" as a group or part of a group refers generally to an optionally substituted aromatic ring having one or more heteroatoms as ring atoms in the aromatic ring with the remainder of the ring atoms being carbon atoms. Suitable heteroatoms include nitrogen, oxygen, sulphur and selenium. Non-limiting examples of heteroaryl include thiophene, benzothiophene, benzofuran, benzimidazole, benzoxazole, benzothiazole, benzisothiazole, naphtho[2,3-b] thiophene, furan, isoindolizine, xantholene, phenoxatine, pyrrole, imidazole, pyrazole, pyridine, pyrazine, pyrimidine, triazine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl.

The term "alkyl" as a group or part of a group refers generally to saturated straight chain, branched or cyclic hydrocarbon groups, such as a $C_1$-$C_{40}$ alkyl, a $C_1$-$C_{30}$ alkyl, or a $C_1$-$C_6$ alkyl. Non-limiting examples of straight chain and branched alkyl include methyl, ethyl, propyl, isopropyl, butyl, sec-butyl, tert-butyl, n-pentyl and branched isomers thereof, n-hexyl and branched isomers thereof, n-heptyl and branched isomers thereof, n-octyl and branched isomers thereof, n-nonyl and branched isomers thereof, and n-decyl and branched isomers thereof. Non-limiting examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl, and the like. An alkyl group may be further optionally substituted by one or more optional substituents as herein defined.

The term "alkenyl" as a group or part of a group refers generally to straight chain, branched or cyclic hydrocarbon residues containing at least one carbon to carbon double bond including ethylenically mono-, di- or poly-unsaturated alkyl or cycloalkyl groups. Non-limiting examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cyclooctatetraenyl, and the like. An alkenyl group may be optionally substituted by one or more optional substituents as herein defined. Where applicable, the substituents on the double bond may be in the E or the Z configuration and, unless expressly stated otherwise, reference herein to an alkene includes both configurations (if applicable).

The term "alkynyl" as a group or part of a group refers generally to straight chain, branched or cyclic hydrocarbon residues containing at least one carbon-carbon triple bond including ethynically mono-, di- or poly-unsaturated alkyl or cycloalkyl groups as previously defined. Non-limiting examples include ethynyl, 1-propynyl, 2-propynyl, butynyl isomers, pentynyl isomers, and the like. An alkynyl group may be further optionally substituted by one or more optional substituents as herein defined.

The term "heterocyclyl" as a group or part of a group refers generally to monocyclic, polycyclic, fused or conjugated hydrocarbon residues wherein one or more carbon atoms (and where appropriate, hydrogen atoms attached thereto) are replaced by a heteroatom so as to provide a non-aromatic residue. Suitable heteroatoms include nitrogen, oxygen, sulphur and selenium. Where two or more carbon atoms are replaced, this may be by two or more of the same heteroatom or by different heteroatoms. Non-limiting examples of heterocyclic groups include pyrrolidinyl, pyrrolinyl, piperidyl, piperazinyl, morpholino, indolinyl, imidazolidinyl, pyrazolidinyl, thiomorpholino, dioxanyl, tetrahydrofuranyl, tetrahydropyranyl, tetrahydropyrrolyl, and the like. A heterocyclyl group may be further optionally substituted by one or more substituents as herein defined.

The term "acyl" as a group or part of a group refers generally to a group containing the moiety C=O (and not being a carboxylic acid, ester or amide). Non-limiting examples of acyl include formyl; straight chain or branched alkanoyl such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl.

The terms alkoxy, alkenoxy, alkynoxy, aryloxy, heteroaryloxy, heterocyclyloxy and acyloxy respectively denote alkyl, alkenyl, alkynyl, aryl, heteroaryl, heterocyclyl and acyl groups as hereinbefore defined when linked by oxygen.

The term thioalkyl refers to an alkyl group when linked by sulfur.

The term "carboxyl" as a group or part of a group refers generally to the group $CO_2H$ and "carboxy ester" as a group or part of a group refers generally to the group $CO_2R$ wherein R is any group not being H.

The term "amino" as a group or part of a group refers generally to the group NRR' and "amido" as a group or part of a group refers generally to the group CONRR', wherein R and R' can independently be H, alkyl, alkenyl, alkynyl, aryl, acyl, heteroaryl, and heterocyclyl.

The term "optionally substituted" as used throughout the specification denotes that a group may or may not be further substituted or fused (so as to form a condensed polycyclic system), with one or more non-hydrogen substituent groups. Preferably the substituent groups are one or more groups independently selected from the group consisting of: halogen (F, Cl, Br, I), =O, =S, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, cyano, nitro, amino, thio, thioalkyl, carboxyl, carboxy ester, amido, keto, acyl, —NHCOO—, —NHCONH—, and —C(=NOH)—Where appropriate, the substituent group may be a terminal group or a bridging group. The substituent group may comprise two or more of the aforementioned groups bonded to one another.

The present invention is particularly concerned with blocking or absorbing UV light having a wavelength of between 280 nm and 380 nm to 400 nm. UVA light has wavelengths between 315 nm and 400 nm, whilst UVB light has wavelengths between 280 nm and 315 nm. Known hazards associated with exposure of the eyes to UV light include eyelid cancer, cataracts, pterygium, keratitis, and macular degeneration. Other effects associated with exposure to UV light are well known. For example, exposure of the skin to UVA and UVB light can lead to sunburn, premature ageing, and skin cancer.

Several regulatory agencies have set standards for UV protection. These include ANSI (The American National Standards Institute), AS (Australian Standard), CEN (European standard), BSI (British Standard) and CSA (Canadian Standards Association). The US Food and Drug Administration have recommended that all glasses, prescription or non-prescription, block 99% of UVB and 95% of UVA.

Regulatory agencies in the United States and Europe consider UVB light to have a wavelength range of 280 nm to 315 nm, and UVA light to have a wavelength range of 315 nm to 380 nm. Therefore, using these criteria, a lens may have to block 95% of UV light of 380 nm to meet the US FDA standards referred to above. However, the Australian Standard designates that UVA light has a wavelength of 315 nm to 400 nm. Therefore, lenses that block 95% of UV light at 380 nm may block considerably less at 400 nm, Accordingly, lens manufacturers are searching for UV-blocking materials that block a greater percentage of light at 400 nm than current materials, without substantially effecting transmittance in the visible spectrum which can give rise to yellowing of a lens. These demands have been particularly difficult to meet in the case of CR-39 lenses. Traditionally, the UV cutoff for CR-39 lenses has been 360 nm because it has not been possible to introduce enough UV absorber into a lens to increase the cutoff value to the 380 nm to 400 nm range without ending up with soft lenses and/or commercially unacceptable yellow lenses.

As previously discussed, the present invention arises from our finding that tris-aryltriazine-based UV absorbers can be incorporated into CR-39 and CR-39/allyl monomer derived lens substrates in amounts sufficient to absorb UV light at 380 nm to 400 nm and still provide a lens of commercially acceptable hardness without commercially unacceptable yellowing. Whilst these developments provide clear benefits in the case of CR-39 lenses, we have also found that the tris-aryltriazine-based UV absorbers provide similar benefits in other plastics that are formed by radical polymerisation. Accordingly, whilst the invention may be discussed in relation to CR-39 lenses, it will be appreciated that the invention is not limited in application to CR-39 lenses and that it can be applied to CR-39/allyl monomer derived lenses as well as other plastic lenses and optical elements.

As discussed previously, the present invention provides an optical element comprising a polymer optical element substrate and a UV absorbing amount of a tris-aryltriazine-based UV absorber incorporated in said substrate. The invention also provides an optical material, the optical material comprising a UV light absorbing amount of a tris-aryltriazine-based UV absorber incorporated in a polymer optical element substrate.

Optical Elements

Whilst the present invention was developed in the context of manufacturing lenses having UV absorbing properties, it will be evident that the methods and compositions described herein could also be used to form other transparent articles in which UV absorption may be required, such as window panes.

In an embodiment of the invention, the optical element is a lens element. The term "lens element" as used herein refers to a finished or unfinished lens or lens blank manufactured from an optically transparent plastic material. A "lens blank" is a lens element that requires some form of treatment, such as cutting a given geometry to deliver a given magnification power, or deposition of a coating. Once all of the cutting and coating steps are completed, the lens blank is termed a "lens".

Optical Element Substrate Monomers

The tris-aryltriazine-based UV absorber can be mixed with one or more of a large number of unsaturated optical element substrate monomers to produce polymer optical element substrates having enhanced UV blocking properties. For ease of polymerisation, the optical element substrate monomer may have reactive ethylenically unsaturated groups. Suitable reactive ethylenically unsaturated groups include (meth)acrylates, olefinic compounds, acrylamides, ethylenically unsaturated amides and urethanes, vinyl esters, vinyl ethers, vinyl halides, vinyl epoxy resins, vinyl silanes and siloxanes, vinyl heterocycles, and prepolymers and polymers of these materials. For ease of polymerisation under radical initiation conditions, (meth)acrylate, allyl, and acrylamide functional groups are preferred As used herein, the term (meth)acrylate is meant to indicate methacrylate or acrylate.

In one embodiment, the polymer optical element substrate is formed by polymerisation of an allyl monomer such as diethylene glycol bisallylcarbonate (CR-39), diallyl phthalate, diallyl isophthalate, diallyl terephthalate, CR-307™ (available from PPG Industries, Inc.), CR-407™ (available from PPG Industries, Inc.), CR-607™ (available from PPG Industries, Inc.), or mixtures thereof.

In another embodiment, the polymer optical element substrate is formed by polymerisation of a (meth)acrylate monomer, such as one or more selected from the group consisting of: mono(meth)acrylates such as methyl (meth)acrylate, n-butyl (meth)acrylate, n-hexyl (meth)acrylate, cyclohexyl (meth)acrylate, 2-ethylhexyl (meth)acrylate, methoxydiethylene glycol (meth)acrylate, methoxypolyethylene glycol (meth)acrylate, 3-chloro-2-hydroxypropyl (meth)acrylate, stearyl (meth)acrylate, lauryl (meth)acrylate, phenyl (meth)acrylate, glycidyl (meth)acrylate, and benzyl methacrylate; mono(meth)acrylates having hydroxyl group(s), such as 2-hydroxyethyl (meth)acrylate, 2-hydroxypropyl (meth)acrylate, 3-hydroxypropyl (meth)acrylate, 3-phenoxy-2-hydroxypropyl (meth)acrylate, and 4-hydroxybutyl (meth)acrylate; di(meth)acrylates such as ethylene glycol di(meth)acrylate, diethylene glycol di(meth)acrylate, triethylene glycol di(meth)acrylate, polyethylene glycol di(meth)acrylate, 1,3-butylene glycol di(meth)acrylate, 1,6-hexanediol di(meth)acrylate, neopentyl glycol di(meth)acrylate, polypropylene glycol di(meth)acrylate, 2-hydroxy-1,3-di(meth)acryloxypropane, 2,2-bis[4-((meth)acryloxy)phenyl]propane (i.e. bisphenol A di(meth)acrylate; SR541), 2,2-bis[4-((meth)acryloxyethoxy)phenyl]propane, 2,2-bis[4-((meth)acryloxy-diethoxy)phenyl]propane, and 2,2-bis[4-((meth)acryloxy-polyethoxy)phenyl]propane; tri(meth)acrylates such as trimethylolpropane trimethacrylate, and tetramethylolmethane trimethacrylate; tetra(meth)acrylates such as tetramethylolmethane tetra(meth)acrylate.

As is known in the art, the optical element substrate monomer may be copolymerised with a comonomer, such as a (meth)acrylate, an acrylate, a vinyl, a vinyl ether, an allyl, an aromatic olefin, an ether, a polythiol, or an epoxy. Specific examples of such comonomers are aromatic vinyl compounds such as styrene, α-methylstyrene, vinyltoluene, chlorostyrene, chloromethylstyrene, and divinylbenzene; mono(meth)acrylates such as methyl (meth)acrylate, n-butyl (meth)acrylate, n-hexyl (meth)acrylate, cyclohexyl (meth)acrylate, 2-ethylhexyl (meth)acrylate, methoxydiethylene glycol (meth)acrylate, methoxypolyethylene glycol (meth)acrylate, 3-chloro-2-hydroxypropyl (meth)acrylate, stearyl (meth)acrylate, lauryl (meth)acrylate, phenyl (meth)acrylate, glycidyl (meth)acrylate, and benzyl methacrylate; mono(meth)acrylates having hydroxyl group(s), such as 2-hydroxyethyl (meth)acrylate, 2-hydroxypropyl (meth)acrylate, 3-hydroxypropyl (meth)acrylate, 3-phenoxy-2-hydroxypropyl (meth)acrylate, and 4-hydroxybutyl (meth)acrylate; di(meth)acrylates such as ethylene glycol di(meth)acrylate, diethylene glycol di(meth)acrylate, triethylene glycol di(meth)acrylate, polyethylene glycol di(meth)acrylate, 1,3-butylene glycol di(meth)acrylate, 1,6-hexanediol di(meth)acrylate, neopentyl glycol di(meth)acrylate, polypropylene glycol di(meth)acrylate, 2-hydroxy-1,3-di(meth)acryloxypropane, 2,2-bis[4-((meth)acryloxyethoxy)phenyl]propane, 2,2-bis[4-((meth)acryloxy-diethoxy)phenyl]propane, and 2,2-bis[4-((meth)acryloxy-polyethoxy)phenyl]propane; tri(meth)acrylates such as trimethylolpropane trimethacrylate, and tetramethylolmethane trimethacrylate; tetra(meth)acrylates such as tetramethylolmethane tetra(meth)acrylate; diallyl phthalate, diallyl isophthalate, diallyl terephthalate.

UV Absorbers

The tris-aryltriazine-based UV absorbers suitable for use with the present invention can be compounds according to Formula (I):

Formula (I)

wherein:
each $Ar^1$, $Ar^2$, and $Ar^3$ is independently selected from the group consisting of: aryl and heteroaryl, each of which may be optionally substituted.

More specifically, the tris-aryltriazine-based UV absorber may be a compound according to Formula (II):

Formula (II)

wherein:
each $R^1$, $R^3$, and $R^5$ is independently selected from the group consisting of:
hydrogen, optionally substituted alkyl, optionally substituted alkenyl, optionally substituted alkynyl, optionally substituted aryl, optionally substituted heteroaryl, optionally substituted heterocyclyl, optionally substituted acyl, optionally substituted alkoxy, optionally substituted alkenoxy, optionally substituted alkynoxy, optionally substituted acyloxy, optionally substituted thioalkyl, carboxyl, carboxy ester, and amido;
each $R^2$, $R^4$, and $R^6$ is independently selected from the group consisting of: hydrogen, halogen (F, Cl, Br, I), optionally substituted alkyl, optionally substituted alkenyl, optionally substituted alkynyl, optionally substituted aryl, optionally substituted heteroaryl, optionally substituted heterocyclyl, acyl, thio, optionally substituted thioalkyl, carboxyl, carboxy ester, amino, amido, cyano, and nitro; and
each m, n, o, w, x, and y is an integer independently selected from the group consisting of 0, 1, 2, 3, 4, and 5, provided that each m+w, n+x, and o+y is an integer selected from the group consisting of 0, 1, 2, 3, 4, and 5.

Even more specifically, the tris-aryltriazine-based UV absorber may be a hydroxylphenyl-tris-aryltriazine derivative according to Formula (III):

Formula (III)

wherein:
each $R^1$, $R^3$, and $R^5$ is independently selected from the group consisting of: hydrogen, optionally substituted alkyl, optionally substituted alkenyl, optionally substituted alkynyl, optionally substituted aryl, optionally substituted heteroaryl, optionally substituted heterocyclyl, acyl, optionally substituted alkoxy, optionally substituted alkenoxy, optionally substituted alkynoxy, acyloxy optionally substituted thioalkyl, carboxyl, carboxy ester, and amido;
each $R^2$, $R^4$, and $R^6$ is independently selected from the group consisting of: hydrogen, halogen (F, Cl, Br, I), optionally substituted alkyl, optionally substituted alkenyl, optionally substituted alkynyl, optionally substituted aryl, optionally substituted heteroaryl, optionally substituted heterocyclyl, acyl, thio, optionally substituted thioalkyl, carboxyl, carboxy ester, amino, amido, cyano, and nitro;
each m, n, w, and x is an integer independently selected from the group consisting of 0, 1, 2, 3, 4, and 5, provided that each m+w and n+x is integer selected from the group consisting of 0, 1, 2, 3, 4, and 5; and
each p and y is an integer independently selected from the group consisting of 0, 1, 2, 3, and 4, provided that p+y is an integer between selected from the group consisting of 0, 1, 2, 3, and 4

In an embodiment of the hydroxylphenyl-tris-aryltriazine derivative according to Formula (III), p is 0, and each $R^5$ is independently selected from the group consisting of: H, alkyl, and -alkyl-C(O)—O-alkyl.

In an embodiment of the hydroxylphenyl-tris-aryltriazine derivative according to Formula (III), each $R^2$ and $R^4$ is independently selected from the group consisting of: aryl, and alkyl. In specific embodiments, $R^2$ and $R^4$ are H, methyl, or phenyl.

In an embodiment of the hydroxylphenyl-tris-aryltriazine derivative according to Formula (III), m and n are 0, and each $R^1$ and $R^3$ is independently selected from the group consisting of: H, alkyl, and -alkyl-C(O)—O-alkyl. In specific embodiments, the alkyl group is a $C_2$ to $C_8$ alkyl group.

In specific embodiments of the invention, the tris-aryltriazine-based UV absorber has one of the following structural formulae:

2-(2,4-diphenyl-1,3-5-triazin-6-yl)-5-(hexyloxy)-phenol (Tinuvin 1577)

2-(2,4-bis(2,4-dimethylphenyl)-1,3-5-triazin-6-yl)-5-(octyloxy)-phenol (Cyasorb 1164)

-continued

Tinuvin 479

2,4-bis(2-hydroxy-4-butoxyphenyl)-6-(2,4-dibutoxyphenyl)-1,3,5-triazine
(Tinuvin 460)

CGL 777

A commercially available UV-absorber available under the trade name Tinuvin 400 may also be used. Tinuvin 400 is similar to Cyasorb 1164, it is a mixture of 2-(4-((2-hydroxy-3-didecyl and tridecyloxypropyl)-oxy)-2-hydroxy phenyl)-4,6-bis(2,4-dimethylphenyl)-1,3,5-triazine.

The amount of tris-aryltriazine-based UV absorber to be incorporated into the polymer optical element substrate varies, depending on the type of optical element substrate monomer used and on the intended UV-absorbing characteristics of the optical element, but may be between about 0.01 and about 2% by weight of the optical element substrate monomer. In an embodiment, the amount of tris-aryltriazine-based UV absorber is between about 0.01 and about 1% by weight of the optical element substrate monomer. In another embodiment, the amount of tris-aryltriazine-based UV absorber is between about 0.04 and about 0.3% by weight thereof.

The tris-aryltriazine-based UV absorber may be dissolved in a solvent and the UV absorber solution mixed with the optical element substrate monomer. Suitable solvents include alcohol, ester, ether or aromatic solvents. Examples of suitable solvents include, but are not limited to, methoxypropyl acetate, 1-methoxy-2-propanol, 2-methoxy-1-methylethyl acetate, toluene and tetrahydrofuran. The concentration of UV absorber in the solution may be between about 10% and about 80% (w/w).

The tris-aryltriazine-based UV absorber may also be used in combination with one or more additional UV absorbers. A variety of UV absorbers are known and/or commercially available and it is envisaged that most of the known absorbers could be used in conjunction with the tris-aryltriazine-based UV absorbers described herein. For example, the additional UV absorber could be a benzophenone or benzotriazole UV absorber. The skilled person is able to find or synthesise benzotriazole or benzophenone derivatives that have UV absorbing qualities and use them without undue experimentation. Some specific examples of benzophenone and benzotriazole UV absorbents that may be suitable include: Ciba Specialty Chemicals Tinuvin P [2-(2'-hydroxy-5'-methylphenyl)benzotriazole]; Cyanamid Cyasorb UV 531 [2-hydroxy-4-n-acetoxy benzophenome]; Cyanamid Cyasorb UV 5411 (2-(2'-hydroxy-5-5-octylphenyl)benzotriazole; 2-(2'-hydroxy-3',6'(1,1-dimethylbenzylphenyl)benzotriazole; 2-(2'-hydroxy-3',5'-di-t-amylphenyl)benzotriazole; bis[2-hydroxy-5-methyl-3-(benzotriazole-2-yl)phenyl]-methane; bis[2-hydroxy-5-t-octyl-3(benzotriazole-2-yl)phenyl]-methane; Cyanamid UV 2098 [2-hydroxy-4-(2-acrylocyloxyethoxy benzophenone]; Cyanamid UV 24 [2,2'dihydroxy-4-methoxy benzophenone]; BASF Uvinul 400 [2,4-dihydroxy benzophenone]; BASF Uvinul D49 [2,2'-dihydroxy 4,4-dimethoxy benzophenone]; BASF Uvinul D50 [2,2',4,4'tetrahydroxy benzophenone]; and the like.

A combination of the tris-aryltriazine-based UV absorber and the additional UV absorber may be dissolved in a solvent such as methoxypropyl acetate, 1-methoxy-2-propanol, 2-methoxy-1-methylethyl acetate, toluene or tetrahydrofuran and the solution mixed with the optical element substrate monomer as previously described.

It is envisaged that for most applications the tris-aryltriazine-based UV absorber will be dissolved in a solvent and the solution mixed with optical element substrate monomer prior to polymerisation. However, it may also be possible for the tris-aryltriazine-based UV absorber and/or the additional UV absorber to be covalently bound to the polymer optical element substrate. Thus, the tris-aryltriazine-based UV absorber and/or the additional UV absorber may be reacted with an optical element substrate monomer and the coupled monomer could then be polymerised to form the polymeric optical element substrate. Alternatively, it may be possible to couple the tris-aryltriazine-based UV absorber and/or the additional UV absorber with polymerised substrate material having pendant reactive groups.

Dyes

It is possible that specific combinations of polymer optical element substrate and tris-aryltriazine-based UV absorber may require a higher than normal amount of the UV absorber in order to achieve an acceptable UV cutoff above 380 nm. It is possible that one has to use so much UV absorber that the optical element also absorbs an amount of light at the upper end of the UVA range and into the visible light range. This may particularly be the case if there is a requirement to obtain the lowest possible % transmittance of UV light at 400 nm. This may result in an observable yellowish tint in the optical element, which is not appealing to consumers.

To counteract yellowing that may result from a higher than normal concentration of tris-aryltriazine-based UV absorber, the optical element may be optionally coloured with a dye to optimise the colour. More specifically, a dye package can be used to hide any yellow colour. The dye can be an organic or an inorganic dye and they may be solvent dyes or dispersion dyes. The dyes can be dissolved or dispersed in the optical element substrate monomer composition. The dye package can be a single colour dye or a mixture of different colour dyes. The dye package can consist of a blue dye and a red dye, or a blue dye and a violet dye. The dyes can be used in the system are organic dyes or inorganic dyes. The dye can be dissolved or dispersed in the monomers. Suitable dyes include, but are not limited to: Sandoplast blue 2B and Solvaperm red BB from Clariant; Microlith blue 4G-A, Orasol blue GN, Orasol blue BL and Orasol red G from Ciba; Kayaset blue A-2R and Kayaset violet A-R from Nippon Kayaku and etc.

Additives and Coatings

For improving scratch resistance, the optical element may be coated with a hard coat, such as an organosilane based hard coat, an acrylate based hard coat, or a hard coat containing inorganic fine particles of tin oxide, silicon oxide, zirconium oxide or titanium oxide.

For improving impact resistance, the optical element may be coated with a primer layer that consists essentially of a polyurethane.

For preventing glare, the optical element may be coated with an anti-reflection layer or stack that contains silicon oxide, titanium dioxide, zirconium oxide, or tantalum oxide. For improving water repellency, the anti-reflection layer or stack may be coated with a water-repellent film of fluoroorganosilane.

The skilled person will be familiar with materials and methods for forming standard coatings on optical elements such as ophthalmic lenses.

Formation of Optical Elements

The present invention provides a method for forming a UV absorbing optical element, the method comprising combining a UV absorbing amount of a tris-aryltriazine-based UV absorbent and an optical element substrate monomer, and polymerising the monomer.

The plastic optical elements are obtained by polymerising a casting composition capable of being polymerised to form a UV absorbing optical element. The casting composition comprises an optical element substrate monomer, and a UV absorbing amount of a tris-aryltriazine-based UV absorber.

Specifically, an optical element substrate monomer (or mixture of comonomers in the case of copolymerisation), such as any one of the substrate monomers mentioned previously, is mixed with the required amount of tris-aryltriazine-based UV absorbent and a polymerisation initiator. The resulting mixture is cast into a mould, such as a mould for lenses, and heated to give the intended plastic optical element. Internal lubricants, antioxidants and any other auxiliary agents could also be added to the casting composition prior to polymerisation.

The casting composition may be polymerised by curing using suitable polymerisation initiators, The initiator may be any of the suitable thermal, chemical and/or photo-initiators known in the art. The nature of the initiator utilised in the composition is dependent upon the ethylenically unsaturated material used. For example, for those ethylenically unsaturated materials that undergo free radical polymerisation, suitable initiators are compounds that liberate or generate a free-radical on addition of energy. Such initiators include peroxy, azo, and redox systems each of which are well known and are described in polymerisation art.

Included among the free-radical initiators are the conventional heat activated catalysts such as organic peroxides and organic hydroperoxides. Examples of these catalysts are benzoyl peroxide, diisopropyl peroxydicarbonate (IPP), dicyclohexyl peroxydicarbonate, tertiary-butyl perbenzoate, cumene hydroperoxide, and azobis(isobutyronitrile). A number of photoinitiators are known in the polymerisation art and may be suitable for use with the present invention.

DESCRIPTION OF EMBODIMENTS OF THE INVENTION

Examples of materials and methods for use with the compositions and methods of the present invention will now be provided. In providing these examples, it is to be understood that the specific nature of the following description is not to limit the generality of the above description.

The physical properties of the plastic lenses produced herein were measured according to standard methods. The UV/Vis spectra of the lenses were recorded with a Varian Cary 500 Scan UV/Vis spectrophotometer. The yellowness indexes (YI) of the lenses were measured with a Hunter Lab UltraScan XE Spectrophotometer

Example 1

0.05, 0.1, 0.15 and 0.2 g of the UV absorber CGL777MPA-D was mixed with 100 g of CR-39 respectively for twenty minutes. Then 3 g of initiator IPP was added to each mix and stirred for ten minutes. The monomer mixes were then filtered and degassed for 30 minutes before filling into the mould assemblies. The lenses were cured in a typical CR-39 curing cycle as follows:
  Start at an oven temperature of 40° C.
  Gradually increase the oven temperature to 52° C. over a 9 hour period
  Then increase the oven temperature to 80° C. over an 11 hour period
  Hold at 80° C. for 1 hour
  Cool to 75° C. over a 15 minute period
  Hold at 75° C. for mould opening.

The mould assemblies were then opened to give the required lenses.

Figure 1:
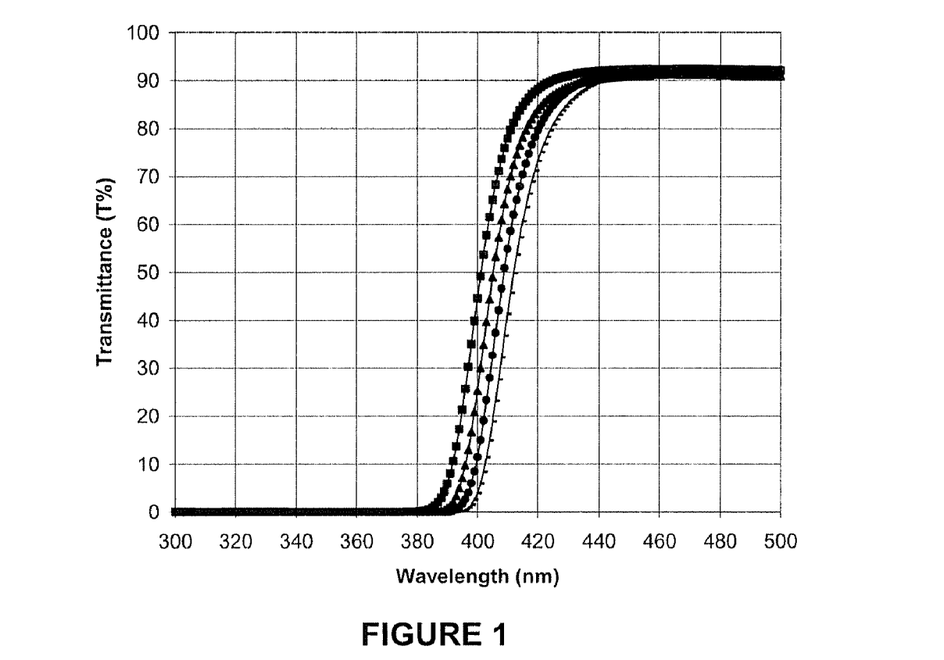
FIG. 1 is a plot of wavelength (nm) vs transmittance (T %) for four CR-39 lenses prepared according to Example 1. 0.05% CGL777MPA-D (■); 0.10% CGL777MPA-D (▲); 0.15% CGL777MPA-D (●); 0.20% CGL777MPA-D (-).

The transmittance was measured on the 2 mm thick 6 based plano lens and is shown in FIG. 1. The yellow index (YI) values for each lens were:

| CGL777 MPA-D | YI |
| --- | --- |
| 0.05% | 1.31 |
| 0.10% | 1.82 |
| 0.15% | 2.57 |
| 0.20% | 3.33 |

Example 2

0.01, 0.05 and 0.1 g of the UV absorber Tinuvin 479 were mixed with 100 g of CR-39 for twenty minutes respectively. Then 3 g of initiator IPP was added into each mix and stirred for ten minutes. The monomer mixes were then filtered and degassed for 30 minutes before filling into the mould assemblies. The lenses were cured in a typical CR-39 curing cycle as in Example 1, and the mould assemblies were opened to give the required lenses.

Figure 2:
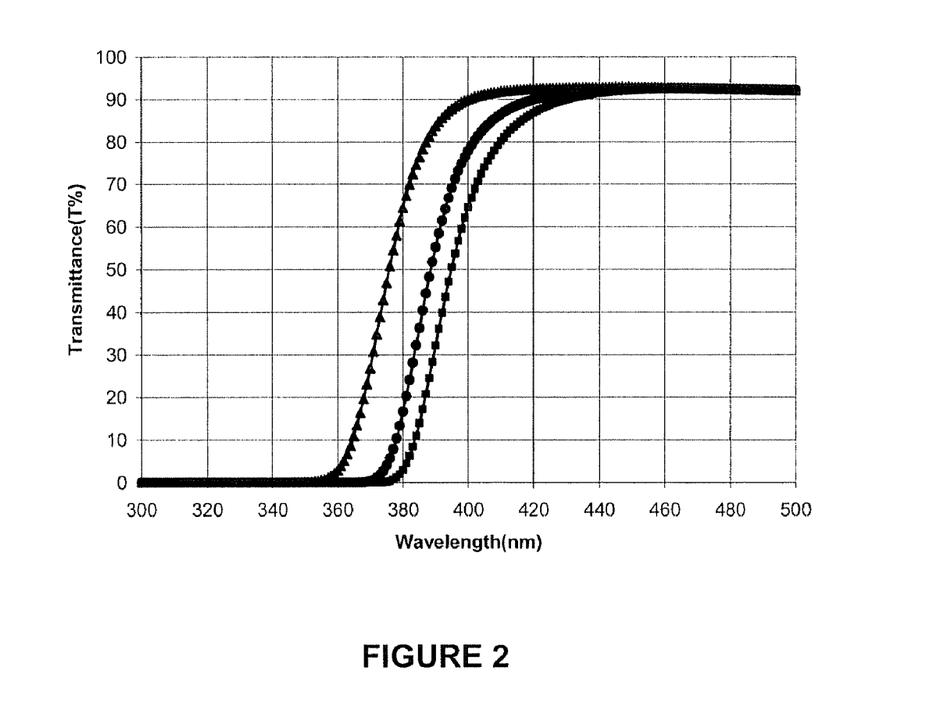
FIG. 2 is a plot of wavelength (nm) vs transmittance (T %) for three CR-39 lenses prepared according to Example 2. 0.01% Tinuvin 479 (▲); 0.05% Tinuvin 479 (●); 0.10% Tinuvin 479 (■).

The transmittance was measured on the 2 mm thick 6 based plano lens and is shown in FIG. 2. The yellow index (YI) values for each lens were:

| Tinuvin 479 | YI |
| --- | --- |
| 0.01% | 0.72 |
| 0.05% | 1.38 |
| 0.10% | 2.25 |

Example 3

0.06 g of the UV absorber Tinuvin 5236 and 100 g of CR-39 were mixed for twenty minutes. Then 3 g of initiator IPP was added and stirred for ten minutes. The monomer mix was then filtered and degassed for 30 minutes before filling into the mould assembly.

The lenses were cured in a typical CR-39 curing cycle as in Example 1, and the mould assembly was opened to give the required lens.

Figure 3:
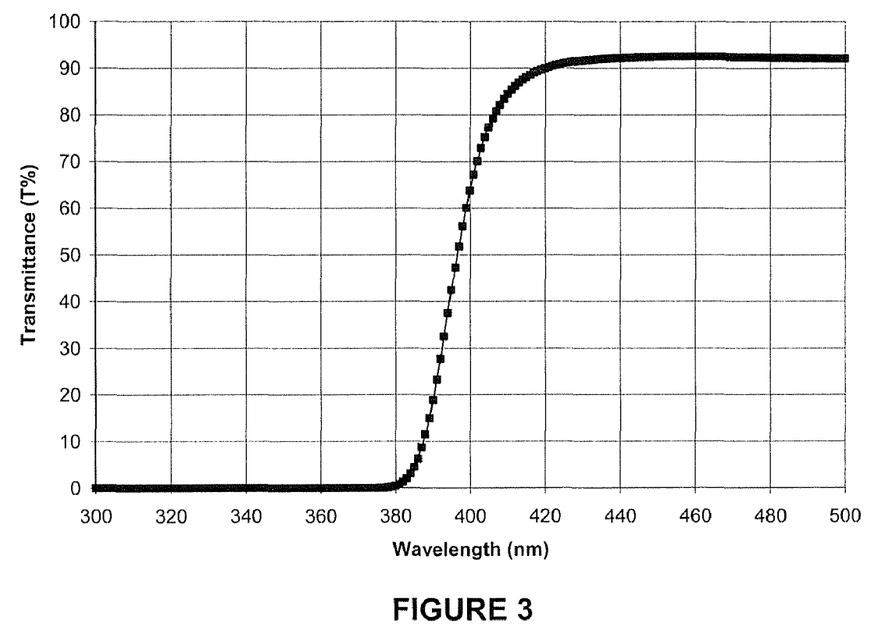
FIG. 3 is a plot of wavelength (nm) vs transmittance (T %) for a CR-39 lens prepared according to Example 3.

The transmittance was measured on the 2 mm thick 6 based plano lens and is shown in FIG. 3. The yellow index (YI) value of this lens was 1.50.

Example 4

0.1 g of the UV absorber Tinuvin 5236 and 100 g of CR-39 were mixed for twenty minutes. Then 3 g of initiator IPP was added and stirred for ten minutes. The monomer mix was then filtered and degassed for 30 minutes before filling into the mould assembly. The lenses were cured in a typical CR-39 curing cycle as in Example 1, and the mould assembly was opened to give the required lens.

Figure 4:
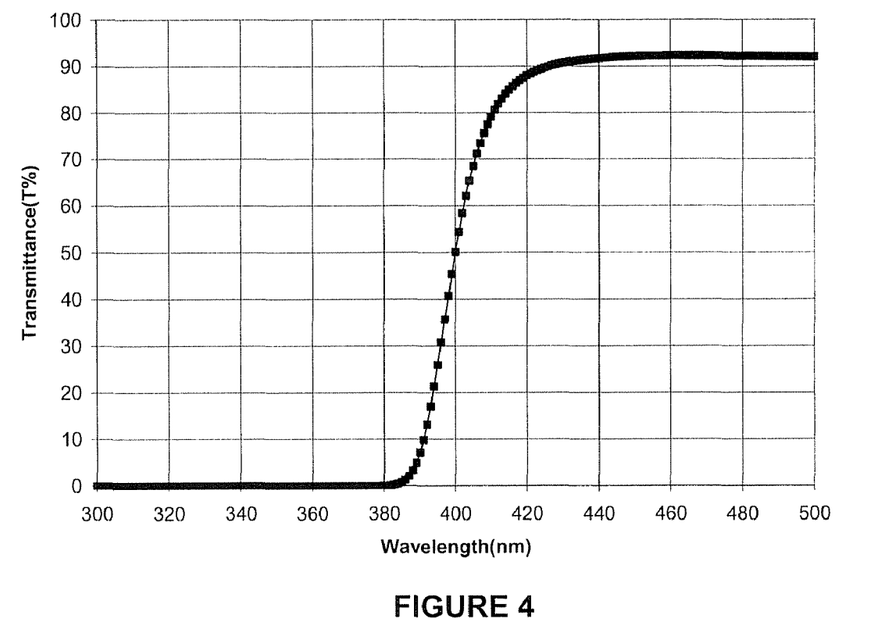
FIG. 4 is a plot of wavelength (nm) vs transmittance (T %) for a CR-39 lens prepared according to Example 4.

The transmittance was measured on the 2 mm thick 6 based plano lens and is shown in FIG. 4. The yellow index (YI) value of this lens was 2.02.

Example 5

0.06 g of the UV absorber CGL777MPA-D, 0.02 g blue dye concentrate and 100 g of CR-39 were mixed for twenty minutes. The blue dye concentrate is a 2% solution of blue dye in CR-39. Then 3 g of initiator IPP was added and stirred for ten minutes. The monomer mix was then filtered and degassed for 30 minutes before filling into the mould assembly. The lenses were cured in a typical CR-39 curing cycle as in Example 1, and the mould assembly was opened to give the required lens.

Figure 5:
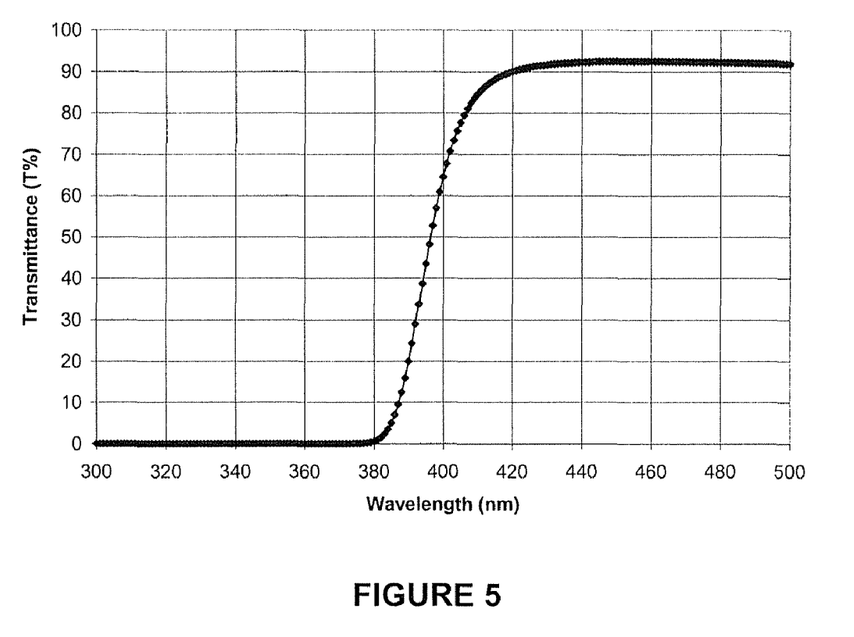
FIG. 5 is a plot of wavelength (nm) vs transmittance (T %) for a CR-39 lens with blue dye prepared according to Example 5.

The transmittance was measured on the 2 mm thick 6 based plano lens and is shown in FIG. 5. The yellow index (YI) value of this lens was 0.46.

Example 6

0.06 g of the UV absorber Tinuvin 5236, 50 g ethoxylated bisphenol A dimethacrylate SR541 and 50 g polyethylene glycol (200) diacrylate were mixed by stirring for 30 minutes. 0.6 g of initiator Trigonox 21 was added and stirred for another 30 minutes.

After filtering and degassing for 60 minutes, the monomer was filled in the mould assembly. After curing in the oven for 21 hours, the assembly was cooled down and opened to give the required lens.

Figure 6:
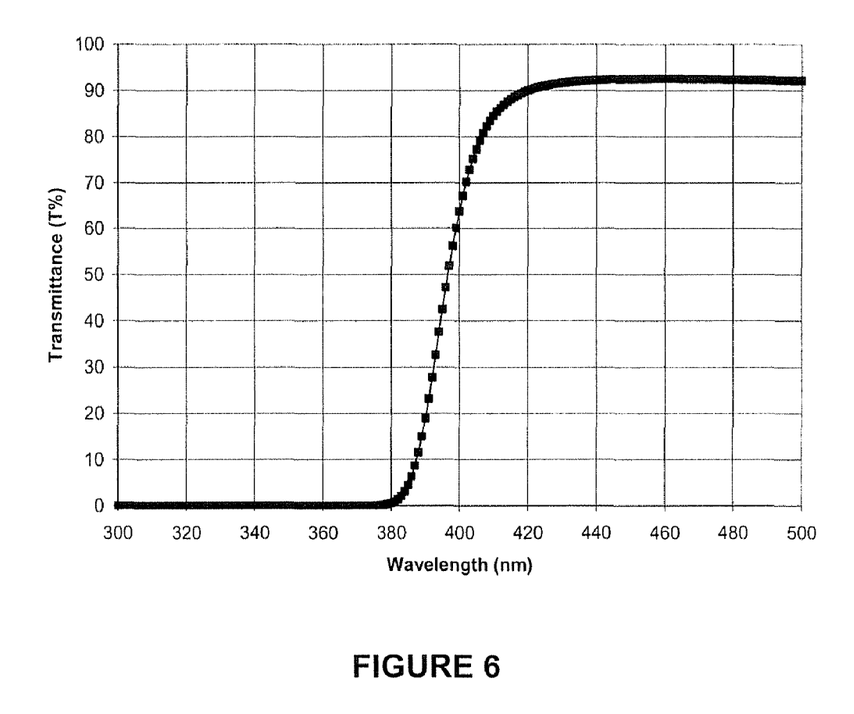
FIG. 6 is a plot of wavelength (nm) vs transmittance (T %) for an acrylate lens prepared according to Example 6.

The transmittance was measured on the 2 mm thick 6 based plano lens and is shown in FIG. 6. The yellow index (YI) value of this lens was 1.46.

Example 7

5 g of Tinuvin 460 was dissolved in 10 g toluene for 1 hour to give an UV absorbent concentrate.

0.09, 0.12, 0.15, 0.18 and 0.21 g of the UV absorbent concentrate was mixed with 100 g of CR-39 respectively for twenty minutes. Then 3 g of initiator IPP was added to each mix and stirred for ten minutes. The monomer mixes were then filtered and degassed for 30 minutes before filling into mould assemblies. The lenses were cured in a typical CR-39 curing cycle as in Example 1, and the mould assemblies were opened to give the required lenses. The UV absorbent concentrations achieved in the lenses were 0.03%, 0.04%, 0.05%, 0.06% and 0.07%.

Figure 7:
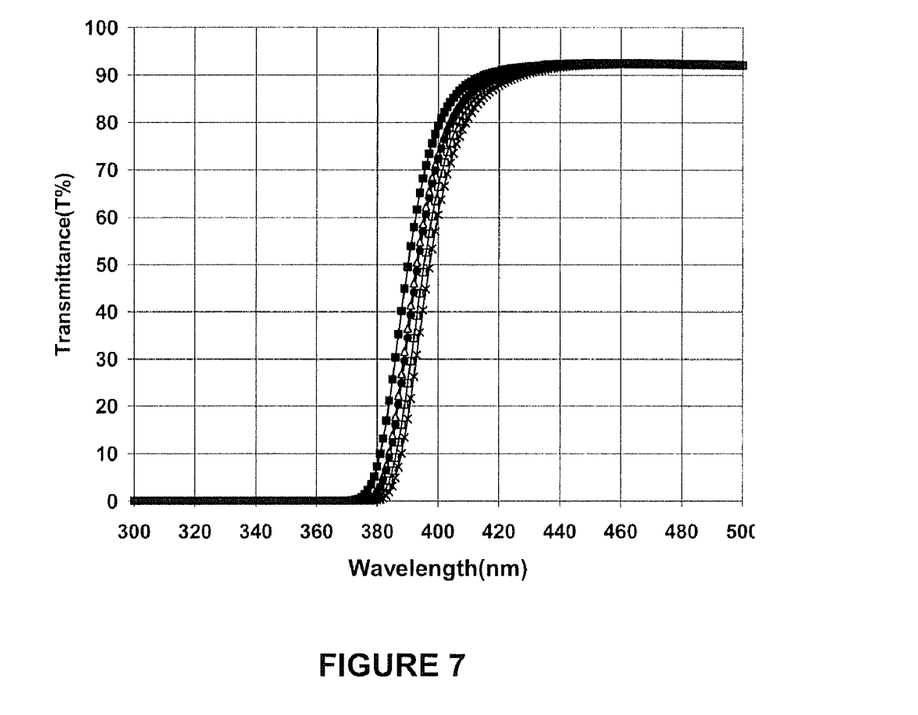
FIG. 7 is a plot of wavelength (nm) vs transmittance (T %) for an acrylate lens prepared according to Example 7. 0.03% Tinuvin 460 (m); 0.04% Tinuvin 460 (Δ); 0.05% Tinuvin 460 (●); 0.06% Tinuvin 460 (□); 0.07% Tinuvin 460 (x).

The transmittance was measured on the 2 mm thick 6 based plano lens and is shown in FIG. 7. The yellow index (YI) values for each lens were:

| Tinuvin 460 | YI |
|---|---|
| 0.03% | 1.11 |
| 0.04% | 1.38 |
| 0.05% | 1.44 |
| 0.06% | 1.74 |
| 0.07% | 2.03 |

Comparative Example 1

100 g of CR-39 and 3 g of initiator IPP was mixed for ten minutes. The monomer mix was filtered, degassed for 30 minutes and filled into the mould assembly. The lens was Cured in a typical CR-39 curing cycle as in Example 1, and the mould assembly was opened to give the required lens.

Figure 8:
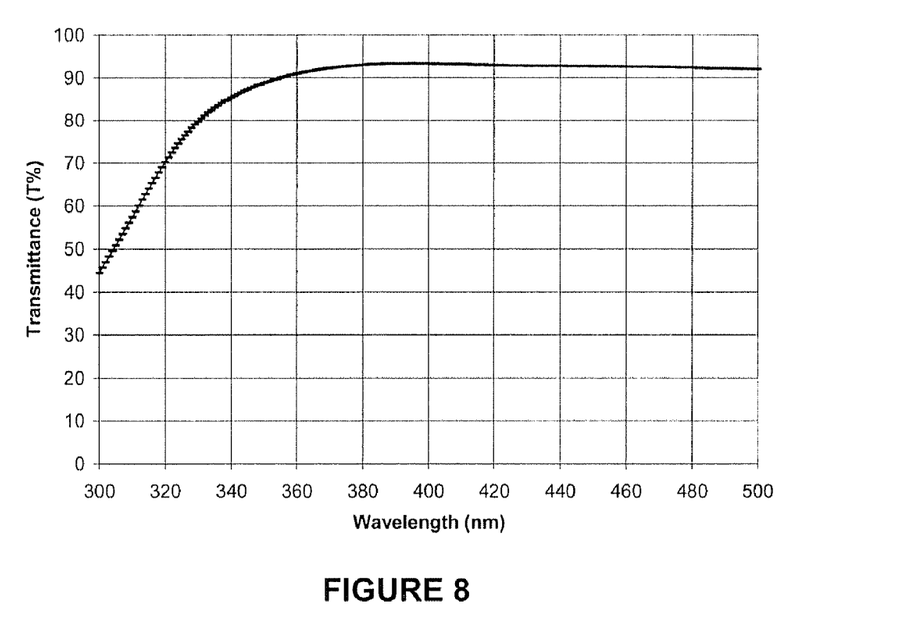
FIG. 8 is a plot of wavelength (nm) vs transmittance (T %) for a CR-39 lens prepared according to Comparative Example 1.

The transmittance was measured on the 2 mm thick 6 based plano lens and is shown in FIG. 8. The yellow index (YI) value of this lens was 0.53.

Comparative Example 2

2,2'-dihydroxy-4-methoxy benzophenone (Cyasorb UV24)

0.06 g of the benzophenone UV absorber Cyasorb UV24 and 100 g of CR-39 were mixed for twenty minutes. Then 3 g of initiator IPP was added and stirred for ten minutes. The monomer mix was then filtered and degassed for 30 minutes before filling into the mould assembly. The lens was cured in a typical CR-39 curing cycle as in Example 1, and the mould assembly was opened to give the required lens.

The transmittance of the Cyasorb UV24 lens is compared with the transmittance of an equivalent lens containing Tinuvin 5236 (see Example 3).

Figure 9:
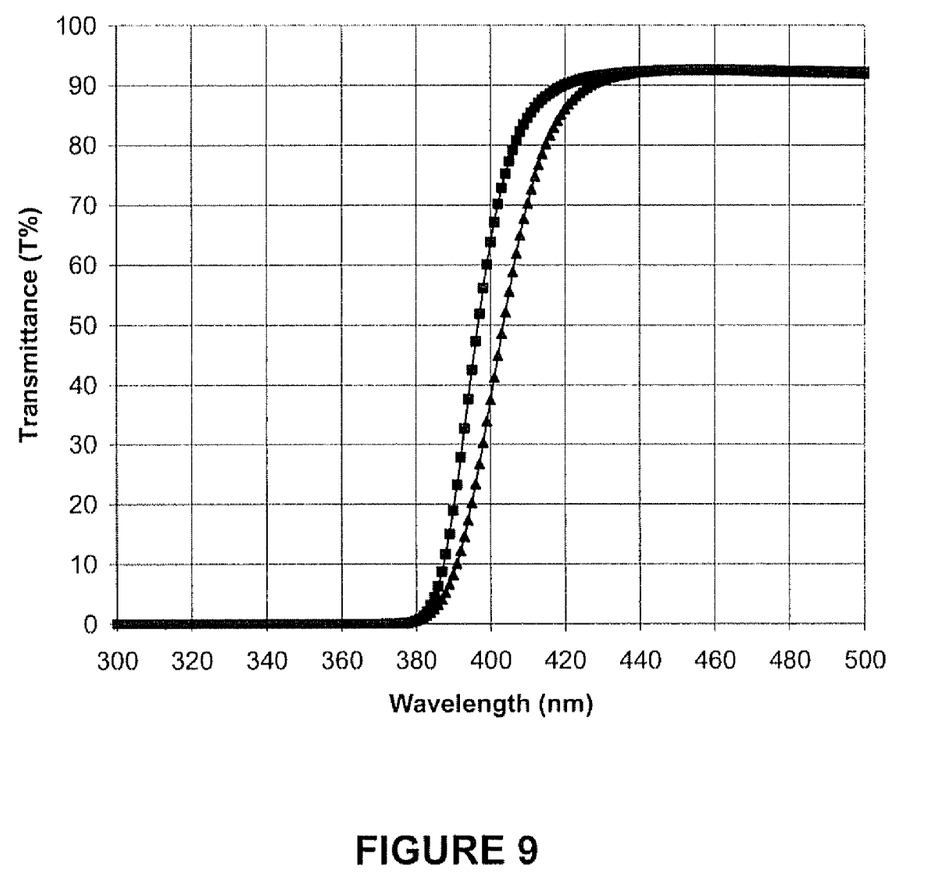
FIG. 9 is a plot of wavelength (nm) vs transmittance (T %) for two CR-39 lenses prepared according to Comparative Example 2. 0.06% Cyasorb UV24 (Δ); 0.06% Tinuvin 5236 (■).

The transmittance was measured on 2 mm thick 6 based plano lenses and is shown in FIG. 9. The yellow index value of the lens with 0.06% Tinuvin 5236 was 1.50; the yellow index value of the lens with 0.06% Cyasorb UV24 was 1.82.

Finally, it will be appreciated that various modifications and variations of the methods and compositions of the invention described herein will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are apparent to those skilled in the art are intended to be within the scope of the present invention.

The invention claimed is:

1. A UV absorbing optical element comprising a spectacle or sunglass polymer optical lens element substrate formed from an allyl monomer, and a UV light absorbing amount of a tris-aryltriazine-based UV absorber according to the following formula:

Formula (II)

wherein:
$R^1$ to $R^6$ are independently selected from the group consisting of: hydrogen, optionally substituted alkyl, optionally substituted alkenyl, optionally substituted alkynyl, optionally substituted aryl, optionally substituted heteroaryl optionally substituted heterocycl, optionally substituted acyl, optionally substituted alkoxy, optionally substituted alkenoxy, optionally substituted alkynoxy, optionally substituted acyloxy, optionally substituted thioalkyl, carboxyl, carboxy ester, and amido;
wherein at least two of $R^1$ to $R^6$ are hydrogen.

2. A UV absorbing optical lens element according to claim 1, wherein the tris-aryltriazine-based UV absorber has the following structural formula:

3. A UV absorbing optical lens element according to claim 1, wherein the polymer optical lens element substrate is formed from an allyl optical element lens substrate monomer and one or more monomers selected from the group consisting of: (meth)acrylate, acrylamide, and mixtures of any two or more thereof.

4. A UV absorbing optical lens element according to claim 3, wherein the polymer optical lens element substrate is formed from a diethylene glycol bisallylcarbonate substrate monomer.

5. A UV absorbing optical lens element according to claim 3, wherein the polymer optical lens element substrate is formed from an optical lens element substrate monomer comprising:
diethylene glycol bisallylcarbonate monomer; and
one or more monomers selected from the group consisting of diallyl phthalate, diallyl isophthalate, and diallyl terephthalate.

6. A UV absorbing optical element according to claim 1, wherein the amount of tris-aryltriazine-based UV absorber is between about 0.01 and about 1% by weight of the optical element substrate monomer.

7. A UV absorbing optical lens element according to claim 1, wherein the UV absorbing amount of a tris-aryltriazine-based UV absorber is sufficient to absorb long-wave UV light having a wavelength of from 300nm up to 380-400 nm.

8. A UV absorbing optical lens element according to claim 1, wherein the % transmittance of light having a wavelength of 380 nm for a 2 mm thick sample of the optical lens element is less than 20%.

9. A UV absorbing optical element according to claim 1, wherein the optical element contains a dye or a dye package.

10. A UV absorbing optical lens element according to claim 9, wherein the dye package comprises a mixture of a blue dye and a red dye, or a mixture of a blue dye and a violet dye.

11. A UV absorbing optical lens element according to claim 1, wherein the lens element is an ophthalmic lens.

12. A UV absorbing optical lens element according to claim 1, wherein the tris-aryltriazine-based UV absorber has the following structural formula:

13. A method for forming a spectacle or sunglass UV absorbing optical lens element, the method comprising combining an allyl optical lens element substrate monomer and a UV absorbing amount of a tris-aryltriazine-based UV absorber according to the following formula:

Formula (II)

wherein:
R$^1$ to R$^6$ are independently selected from the group consisting of: hydrogen, optionally substituted alkyl, optionally substituted alkenyl, optionally substituted alkynyl, optionally substituted aryl, optionally substituted heteroaryl, optionally substituted heterocyclyl, optionally substituted acyl, optionally substituted alkoxy, optionally substituted alkenoxy, optionally substituted alkynoxy, optionally substituted acyloxy, optionally substituted thioalkyl, carboxyl, carboxy ester, and amido;
wherein at least two of R$^1$ to R$^6$ are hydrogen.

14. A method according to claim 13, wherein the tris-aryltriazine-based UV absorber has the following structural formula:

15. A method according to claim 13, wherein the allyl optical lens element substrate monomer is mixed with a monomer selected from the group consisting of: (meth)acrylate, acrylamide, and mixtures of any two or more thereof.

16. A method according to claim 15, wherein the optical lens element substrate monomer is diethylene glycol bisallylcarbonate.

17. A method according to claim 15, wherein the optical lens element substrate monomer comprises:

diethylene glycol bisallylcarbonate monomer; and one or more monomers selected from the group consisting of diallyl phthalate, diallyl isophthalate, diallyl terephthalate.

18. A method according to claim 13, the method further comprising introducing the mixture into a mold for a lens before polymerising the optical lens element substrate monomer.

19. A method according to claim 13, wherein the tris-aryltriazine-based UV absorber has the following structural formula:

* * * * *